United States Patent [19]
DeLeonardis

[11] Patent Number: 5,800,425
[45] Date of Patent: Sep. 1, 1998

[54] AUTOMATIC NASAL ASPIRATORS

[76] Inventor: Rocco J. DeLeonardis, P.O. Box 3093, McLean, Va. 22103

[21] Appl. No.: 697,593

[22] Filed: Aug. 27, 1996

Related U.S. Application Data

[60] Provisional application No. 60/002,843 Aug. 28, 1995.
[51] Int. Cl.⁶ ................................................. A61M 1/00
[52] U.S. Cl. ................................... 604/27; 600/573
[58] Field of Search .............................. 128/760, 763, 128/765, 768, 769; 604/27, 35, 36, 37, 54, 93, 212; 600/573, 574, 578, 581

[56] References Cited

U.S. PATENT DOCUMENTS

| | | |
|---|---|---|
| 2,575,513 | 11/1951 | Fox. |
| 3,833,001 | 9/1974 | Abrahams et al. |
| 4,068,664 | 1/1978 | Sharp et al. |
| 4,684,362 | 8/1987 | Holt .................................... 604/54 |
| 5,009,635 | 4/1991 | Scarberry ............................ 604/27 |

FOREIGN PATENT DOCUMENTS 1136-018   11/1982   Canada.

*Primary Examiner*—Michael Powell Buiz
*Assistant Examiner*—William Lewis
*Attorney, Agent, or Firm*—Law Firm of Naren Thappeta

[57] ABSTRACT

An automatic nasal aspirator for cleaning matter in the nasal canal of an infant. The aspirator includes a collection member for collecting the cleaned matter. The collection member is designed for insertion into the nasal canal. The aspirator further includes a hose having a first end and a second end with the first end being removably connected to the collection member. A motor is connected to the second end of the hose. The motor imparts a suction action to the collection member through the hose, wherein the suction action causes the matter to be cleaned from the nasal canal and collected in the collection member.

8 Claims, 1 Drawing Sheet

AUTOMATIC NASAL ASPIRATORS

CROSS-REFERENCE TO RELATED APPLICATIONS

The present application claims priority from Provisional application Ser. No. 60/002,843 entitled "Automatic Nasal Aspirator" filed Aug. 28, 1995.

1. Field of the Invention

The present invention relates to nasal aspirators and more particularly to a portable nasal aspiration device which is provided with a motor for automatic suction of the nasal passages for infants.

2. Related Art

When an infant has a respiratory infection or even an ordinary cold, its nasal passages often become blocked due to a build-up of mucous. The accumulation of mucous can make it difficult for the child to rest or even eat properly. It is virtually impossible for a nursing or bottle-feeding infant to eat when its nasal passages are congested. In addition, the mucous which is allowed to remain in the nasal passages can drain through the back of the throat into the lungs, causing further infection.

Because infants are not capable of expressing the built-up mucous on their own, it is necessary for a caregiver to manually aspirate the child's nasal passages in order to removal the mucous therefrom. The aspiration is most often accomplished by using a device known as a bulb syringe. By squeezing the bulb syringe, which is hollow and formed of rubber-like material, air is evacuated from the interior of the syringe. The syringe is then inserted into the nasal passages of the child and the built-up mucous is drawn into the interior of the device.

However, there are numerous problems associated with the use of a manual bulb syringe. Namely, because suction is only imparted for a short time, the bulb syringe must be inserted and removed from the nasal passage numerous times before the passage is adequately cleaned. Such numerous insertions usually aggravate the child who is most likely already irritable and fussy due to being congested. Additionally, there is little or no control over the amount and degree of suction which is being applied by a bulb syringe. These problems are especially acute in the case of certain infections that produce excessive amounts of mucous in children.

When an infant is trying to sleep with a blocked air passage, the parent cannot easily clear the infant's nasal passage without waking the infant because to clear an infant's air passage with the conventional aspirators takes a concerted effort by putting the Aspirator against the infant's nostril and sucking as much mucous out as possible with the small amount of suction air that the Aspirator provides. This motion may need to be repeated for as many as ten to twenty times to clear the passage and it is often impossible to do it without the lights on which adds to the infant's already uncomfortable situation.

Because the bulb syringe is both burdensome to use and irritating to the child, many parents and caregivers may either use the bulb syringe improperly or forego its use altogether, in either case causing the nasal passages to remain at least partially blocked. Although the prior art has made attempts at providing alternate means for removing accumulated mucous, none have proved to be adequate.

For example, U.S. Pat. No. 3,833,001 to Abrahams et al. discloses a demucosant for aspiration and removal of sinus fluids wherein suction power is imparted by water from a faucet. The arrangement of Abrahams et al. may be impractical from the standpoint that the device may always need to be used in the vicinity of a source of water.

Canadian Patent 1,136,018, issued November 1982, teaches a motor driven nose cleaning apparatus which includes a nasal insert and a collection receptacle for receiving and storing mucous which is aspirated from the nasal passages. Although the aspirator of certain embodiments of the Canadian patent is portable, there is no easy way to clean the device. As such, to avoid contamination and pathogen growth, both the collection receptacle and nasal insert must be removed and discarded on a regular basis, most likely, after each use. This can be burdensome and expensive.

Accordingly, there exists a need for an automatic nasal aspirator which is portable, efficient, unintrusive, and adaptable for use with children. In the case of infants, to be truly useful the device must be conveniently portable, e.g., because infants frequently sleep while riding in automobiles and in other locations while traveling.

SUMMARY OF THE INVENTION

The present invention is directed to an Automatic Nasal Aspirator which cleans matter in a nasal canal of an infant. The Automatic Nasal Aspirator includes a collection member for collecting the cleaned matter. The collection member is designed for insertion into the nasal canal. The aspirator further includes a hose having a first end and a second end with the first end being removably connected to the collection member.

A motor is connected to the second end of the hose. The motor imparts a suction action to the collection member through the hose, wherein the suction action causes the matter to be cleaned from the nasal canal and collected in the collection member.

The Automatic Nasal Aspirator may further comprise a filter placed between the hose and the collection member. The filter allows air to pass through while preventing the cleaned matter from entering the hose. Such passing of air allows suction action to be imparted from the motor to the collection member.

The collection member is operable manually to clean the matter from the nasal canal. The collection member is made of resilient material such that the collected cleaned matter can be evacuated by squeezing the collection member. Therefore, even when the motor is inoperable, for example due to malfunctioning, the Automatic Nasal Aspirator of the present invention may be used or aspirating a nasal canal.

Therefore, by using a motor to suck matter from a nasal canal, the Automatic Nasal Aspirator may effectively clean a nasal canal. In addition, by operating the motor at various speeds, the suction power may be varied to suit the particular situation.

By using a collection member which can be operated manually, the Aspirator may be used for clearing a nasal track even when the motor is unavailable. This makes the present invention particularly suited for portable applications.

As the collection member is removable, the apparatus of the present invention may be easily cleaned.

By using a hose of sufficient length, the effect of any sound the motor may generate on the sleep of an infant may be minimized.

By using a filter, the present invention allows suction action to be imparted, but at the same time prevents the collected matter from entering the hose or These and the other features and advantages will be apparent from the following description.

DETAILED DESCRIPTION OF THE PREFERRED EMBODIMENTS

Figure 1:
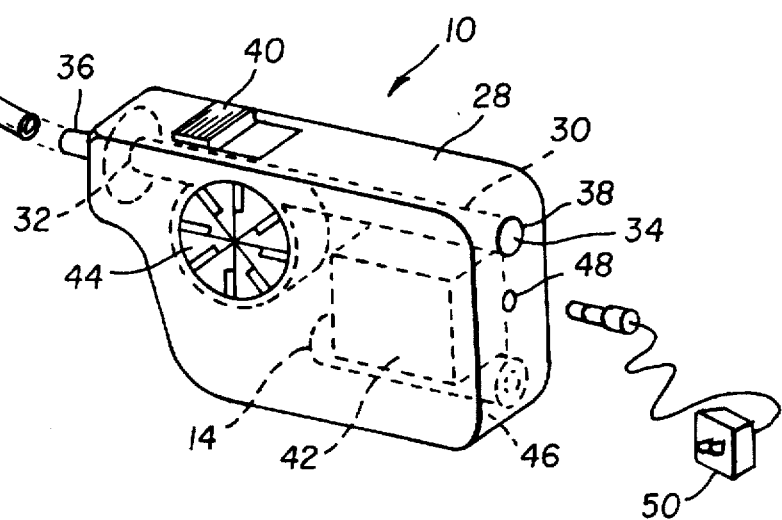
FIG. 1 shows a perspective view in a partial cutaway of an automatic nasal aspirator according to the present invention.

The Automatic Nasal Aspirator of the present invention, indicated generally as 10 in FIG. 1, preferably includes three main components: a hollow collection member 12, a motor assembly 14, and a flexible hose 16 which connects the collection member 12 to the motor assembly 14.

The collection member 12 is preferably of resilient construction and formed of a rubber like material similar to that of a conventional bulb syringe. The collection member 12 may be of any shape. However, it is desirable that the central portion 18 of the collection member be of a larger diameter than either of the ends 20, 22 so that it possesses an adequate capacity to collect all fluid during nasal aspiration, yet any fluid which is collected therein may be readily evacuated by squeezing the central portion 18.

The collection member 12 has a nasal insertion end 20 and a hose connection end 22. The nasal insertion end 20 tapers to a blunt tip and is provided with an aperture which allows mucous to enter the collection member 12. The hose connection end 22 forms a hollow projection and is sized to be receivingly accepted by one end of the hose 16.

The aspiration 10 may also be provided with a cap 24 sized to cover the hose connection end 22, such that the collection device 12 may be removed from the assembly 10 and used manually similar to a conventional aspiration in the event neither batteries nor electricity are available.

Figure 3:
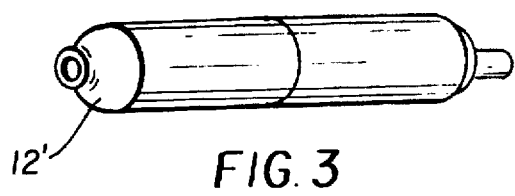
FIG. 3 shows an alternate collection member.

In an alternate embodiment shown in FIG. 3, the nasal aspiration is provided with a cylindrical collection member 12', which has a constant diameter about its length. By providing the aspirator with both collation members 12, 12', the user would have flexibility in deciding which member 12, 12' is best suited for a particular situation.

The hose 16 is preferably formed of plastic and is somewhat flexible. Typical materials include those commonly known to be useful in medical hoses and tubes. The hose 16 should preferably be approximately 2–3 feet in length so as to ensure that the collection member 12 and the motor 14 are sufficiently separated. By separating the motor 14 and collection member 12, aspiration of children's nasal passages can be accomplished with minimal disturbance to the child.

Figure 2:
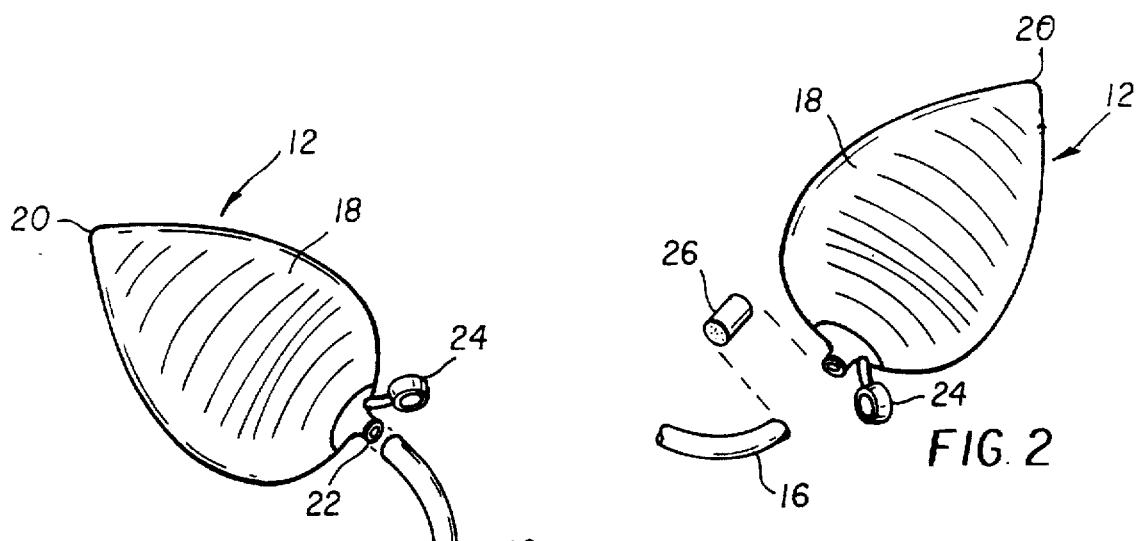
FIG. 2 shows the use of an optional filter.

Although not essential, it is contemplated that a cylindrical filter fitting 26 may be removable provided between the hose connection end 22 of the collection member 12 and the hose 16 as shown in FIG. 2. The filter 26 will allow air to pass through while ensuring that no fluid evacuated from the nasal passages is permitted to enter the hose 16 or the motor assembly 14.

The motor assembly 14 includes an outer housing 28 which is preferably formed of a rigid plastic. Within the housing 28, there is provided a lateral air flow cylinder 30 which terminates at each end thereof at an aperture 32, 34 formed in the housing 28. A first end 36 of the air flow cylinder 30 projects outwardly from the housing 28 and is adapted to receive a terminal end of the hose 16. The opposite end 38 of the cylinder 30 terminates flush with the aperture 34 formed in the housing.

The Aspirator 10 is electrically powered and is provide with both a battery compartment 46 and an outlet 48 for receiving the male end of the optional DC adaptor 50. On the outer surface of the hosing 28, there is provided a switch mechanism 40 which serves to activated and control the speed of a motor 42. The motor 42 propels a suction wheel 44, by creating a movement of air which causes a suction, such that when the hose 16 is attached to the first end 36 of the air cylinder 30, air is drawn inwardly through the collection device 12 and hose 16 and into the motor assembly 14 via the air flow cylinder 30, exiting at its opposite end 38.

When the collection member 12 is inserted within a nasal passage, the suction action imparted by the suction wheel 44 acts to draw any mucous or fluid into the member 12. After the nasal passage is sufficiently cleaned, the collected mucous an be easily discharged from the collection member 12 by squeezing the central portion 18. The collection member 12 can be rinsed with clean water and/or a disinfectant.

It is contemplated that the switch mechanism 44 permit the speed of the suction wheel 40 to be controlled. That is, the switch mechanism 44 allows the user to select either a high or low suction setting as well as an off position. Alternately the switch 44 may have more than two settings which permits even greater selection and control of the suction strength. For instance, if the device is to be used to clean the nose of a sleeping child, it may be wise to select a low suction to decrease the likelihood he or she will awaken. On the other hand, if an infant is severely congested or the mucous consistency is thickened, a high suction strength would be required in order to effectively loosen and remove the mucous and restore a clear breathing passage.

The invention may be embodied in other specific forms without departing from its spirit or essential characteristics. The described preferred embodiments are to be considered in all respects only as illustrative and not restrictive.

What is claimed is:

1. An Automatic Nasal Aspirator to clean matter from a nasal canal, said Automatic Nasal Aspirator comprising:

a collection member for collecting the matter, said collection member having a tapered end for insertion into the nasal canal from where the matter is to be cleaned, said collection member having two ends, wherein said hose is removably connected to one of said two ends and the other end comprises the tapered end, and wherein said second end is not directly connected to any hose like structure such that the tapered end can be used at a point in the nasal canal from where the matter is collected;

a hose having a first end and a second end, the first end being connected to said collection member; and a motor connected to the second end of said hose, said motor imparting a suction action to said collection member through said hose, wherein the suction action causes the matter to be cleaned from the nasal canal and collected in said collection member when said tapered end is inserted into the nasal canal, and wherein the tapered end of the collection member is short such that the suction action need not be of high strength.

2. The automatic Nasal Aspirator of claim 1, wherein said collection member is made of resilient material such that the matter can be cleansed from the nasal canal by squeezing the collection member.

3. The Automatic Nasal Aspirator of claim 2 wherein said collection member is made of resilient material such that the collected cleaned matter can be evacuated by squeezing said collection member.

4. The Automatic Nasal Aspirator of claim 3 wherein said collection member is removably connected to said hose.

5. The Automatic Nasal Aspirator of claim 4, further comprising a filter placed between said hose and said collection member, said filter allowing air to be pass through while preventing the cleaned matter from entering said hose.

6. The automatic nasal aspirator of claim 1, wherein said collection member comprises at bulb, and wherein the bulb has said tapered end.

7. An Automatic Nasal Aspirator to clean matter from a nasal canal, said Automatic Nasal Aspirator comprising:
- a collection member for collecting the matter, said collection member being made of resilient material, collection member being made of resilient material such that the matter can be collected and evacuated by squeezing the collection member;
- a hose removably connected to said collection member; and
- a motor connected to said hose, said motor imparting a suction action to said collection member through said hose, wherein the suction action causes the matter to be cleaned from the nasal canal and collected in said collection member,
- a filter connected between said hose and said collection member, said filter allowing air to pass through while preventing the cleaned matter from entering said hose.

8. An automatic nasal aspirator to clean matter from a nasal canal, said automatic nasal aspirator comprising:
- a collection member for collecting the matter, said collection member being made of resilient material;
- a hose removably connected to said collection member; and
- a motor connected to said hose, said motor imparting a suction action to said collection member through said hose, wherein the suction action causes the matter to be cleaned from the nasal canal and collected in said collection member,
- filter connected between said hose and said collection member, said filter allowing air to pass through while preventing the cleaned matter from entering said hose.

* * * * *